(12) United States Patent
Ko (10) Patent No.: US 7,276,257 B2
(45) Date of Patent: Oct. 2, 2007

(54) SCHISANDRIN B PREPARATION

(75) Inventor: Kam Ming Ko, Kowloon (HK)

(73) Assignee: The Hong Kong University of Science and Technology, Kowloon (HK)

( * ) Notice: Subject to any disclaimer, the term of this patent is extended or adjusted under 35 U.S.C. 154(b) by 47 days.

(21) Appl. No.: 11/188,021

(22) Filed: Jul. 22, 2005

(65) Prior Publication Data

US 2007/0020345 A1 Jan. 25, 2007

(51) Int. Cl.
*A61K 36/79* (2006.01)
(52) U.S. Cl. .................................................. 424/725
(58) Field of Classification Search .................... None
See application file for complete search history.

(56) References Cited

U.S. PATENT DOCUMENTS

| 4,684,628 A | 8/1987 | Liu |
| 5,484,595 A | 1/1996 | Ikeya et al. |
| 6,261,565 B1 * | 7/2001 | Empie et al. ............... 424/757 |
| 6,596,321 B1 | 7/2003 | Yan et al. |
| 6,605,305 B2 | 8/2003 | Zhao |
| 2002/0127189 A1 * | 9/2002 | Myers et al. ................. 424/48 |
| 2005/0119337 A1 * | 6/2005 | Hu .............................. 514/462 |

FOREIGN PATENT DOCUMENTS

| CN | 1415318 A | 5/2003 |
| GB | 2186572 A2 | 8/1987 |
| WO | WO 00/74697 A1 * | 12/2000 |

OTHER PUBLICATIONS

Ko et al. (Phytotherapy Research (1996), vol. 10, pp. 450-452).*
Panossian et al. (Phytomedicine (1999), vol. 6, No. 1, pp. 17-26).*
http://www.amazon.com/Herbal-Traditional-Medicine-Molecular-Oxidative/dp/0824754360—accessed Mar. 22, 2007.*
Kam-Ming Ko et al., Pharmaceutical Biology 2002 vol. 40, No. 4, pp. 298-301, Protection against Carbon Tetrachloride Liver Toxicity by Enantiomers of Schisandrin B Associate.

Kam-Ming Ko, Shengmai San: Traditional Herbal Medicines for Modern Times, vol. 1 2002.
Ji, Yuxia et al., "Preparation and quality evaluation of *Schisandra chinensis* parenteral emulsion"' Zhongguo Yiyuan Yaoxue Zazhi, 2004, 24(11): 713-714, China.
Du, Yingfeng et al. "Determination of deoxyschizandrin and schizandrin B in *Schisandra chinensis* and Weiganfutai tablets by RP-HPLC" Zhongcaoyao, 2004, 35 (5): 519-521, China.
He, Yanping et al. "Quantitative analysis of γ-schizandrin in Manganbao granules, A complex prescription of Chinese medicine". Zhongguo Zhongyao Zazhi, 1995, 20(9): 541-2, China.
Cui, Langui et al. "Determination of deoxyschizandrin and schisandrin B in Gengnianan tablets by HPLC", Zhongcaoyao, 2001, 32(5): 409-411, China.
Zhong, Zhaoqing et al. "HPLC determination of schizandrin B in Livoprotect tablets.". Zhongcaoyao, 1996, 27(4):215-216, China.
Liu, Qunfeng et al. "Simultaneous determination of schizandrin A and B in Gandeining pill by HPLC", Zhongguo Zhongyao Zazhi, 2000, 25(3): 157-158, China.
Tian, Gengcun et al. "The preparation, pharmacology and clinical application of Shengmaisan"' Chinese Traditional Patent Medicine, 2000; 22(2): 162-165.
Ko, RKM, and Mak, DHF: "Schisandrin B and other Dibenzocyclooctadiene lignans. In: Herbal and Traditional Medicine: Molecular Aspects of Health." Packer L, Halliwell B, Ong CN, editors. Marcel Dekker: New York, Basel, Hong Kong, 2004, pp. 289-314.

* cited by examiner

*Primary Examiner*—Susan Coe Hoffman
(74) *Attorney, Agent, or Firm*—Ryan A. Schneider, Esq.; Troutman Sanders LLP (57) ABSTRACT

The present invention provides a preparation for treatment or prevention of a condition in a patient, said preparation comprising Schisandrin B. The concentration of Schisandrin B in the preparation may be between about 0.01 and about 0.1%, or it may be between about 20 and about 40% w/w or w/v. The preparation may additionally comprise one or more components selected from the group consisting of herbal extracts, fluids, solvents, antioxidants, preservatives, electrolytes, salts and pH control agents.

8 Claims, 3 Drawing Sheets

(iii)

(iii)

Fig. 2B

SCHISANDRIN B PREPARATION

TECHNICAL FIELD

The present invention relates to preparations comprising Schisandrin B, to methods for making the preparations, and to methods for prevention and/or treatment of heart disease or other conditions using the preparations.

BACKGROUND OF THE INVENTION

Physical exercise is generally beneficial to health by enhancing body metabolism and improving heart-lung function as well as muscle endurance. One fact that is unknown to many people is the potential harmful effect produced by unaccustomed exercise due to the insufficiency in heart-lung function. When the heart-lung function is adequate for the exercise or the loss of body fluid from profuse sweating is not quickly replenished, the muscle may be injured and the heart-lung function may suffer instead of becoming healthier after exercise.

Shengmai San (SMS), a Chinese medicine formula comprising Ginseng root, *Schisandra* fruit and Ophiopogonis root, was first cited in Chinese medical literature in 1247 AD. According to Chinese medicine theory, SMS, which can invigorate the Qi and preserve body fluid, is prescribed for Qi and Yin deficiency, particularly during the hot summer period when profuse sweating commonly occurs. Traditionally, SMS is used for the treatment of excessive loss of essence-Qi and body fluid that threaten heart failure. According to the symptom differentiation of Chinese medicine, patients suffering from coronary heart disease show a prevalence of Qi and Yin deficiency, a condition strongly indicated for SMS. SMS, which restores blood volume and prevents myocardial infarction, can also be prescribed for patients with coronary heart disease.

In terms of modern medicine, SMS can enhance adaptation to stress, transformation of nutrients and oxygen into energy, oxygenation of tissues, and prevent dehydration. All these effects are beneficial for individual performing physical exercise during sports activities. Nevertheless, current sports drinks and drugs used for the prevention and treatment of coronary heart disease are not designed for enhancing the heart-lung function, which is a crucial factor in improving physical performance and in recovery from coronary heart disease.

There is a need for a preparation that can be readily administered to an individual, preferably orally, which is capable of enhancing the heart-lung function as well as preventing and/or treating cardiovascular conditions or other conditions.

OBJECT OF THE INVENTION

It is the object of the present invention to at least partially satisfy the above need.

SUMMARY OF THE INVENTION

In a first aspect of the invention there is provided a preparation for treatment or prevention of a condition in a patient, said preparation comprising Schisandrin B. The preparation may be suitable for oral administration to a patient. It may be ingestible, and may be drinkable. It may be non-toxic to a patient to which it is administered. The preparation may comprise Shisandrin B isolated from plant matter, for example a *Schisandra* plant, such as *Schisandra chinensis* (*Fructus schisandrae*), or it may comprise plant matter, or an extract thereof, containing Schisandrin B, or it may comprise both. Alternatively or additionally the Schisandrin B may be synthetic, and may be produced using a chemical or biochemical synthesis process (e.g. a process involving organisms produced using recombinant, mutagenic or other methods). The Schisandrin B may be the (−) isomer. Schisandrin B may be dissolved, suspended, dispersed or emulsified in the preparation. In addition, the preparation may comprise one or more other components, for example herbal extracts, fluids, solvents (e.g. water), antioxidants, preservatives, pH control agents or other additives. These may be non-toxic. They may be pharmaceutically acceptable. The preparation may be liquid, and may be an aqueous preparation. It may be a solvent based preparation, for example an ethanolic preparation, a tincture or some other solvent based preparation. The preparation may be a drink, for example a sports drink, or it may be a pharmaceutical preparation. The pharmaceutical preparation may be a liquid, or a powder or it may be in some other form. The preparation may additionally comprise other beneficial components, for example electrolytes, salts etc. The condition may be a heart condition, or a condition of some other organs for example liver, kidney or lung. The condition may be a cardiovascular condition, myocardial damage or infarction, coronary heart disease, impaired heart-lung function, cancer, heart failure, ischaemia, viral myocarditis, septic/hemorrhagic shock, liver failure, chronic hepatitis, chronic bronchitis, gastritis, type II diabetes, toxic side effects arising from cancer chemotherapy, aging and age-related diseases such as liver and heart failure, Alzheimer's disease, Parkinson's disease, dehydration or failure of other organs. The condition may be muscle damage, for example exercise induced muscle damage.

In one embodiment the preparation comprises:
Saponins (e.g. ginsenosides derived from Ginseng), and
Lignans (derived from *Schisandra* ), including Schisandrin B.

The saponins may be ginsenosides. The saponins may be present between about 0 and about 3%, or between about 0.6 and about 1.5% w/w or w/v. They may be present at about 0.6% w/v. The lignans may be present between about 0.05 and about 0.5%, or between about 0.1 and about 0.2% w/w or w/v. They may be present at about 0.1% w/v. Schisandrin B may be present between about 0.01 and about 0.1%, or between about 0.02 and about 0.04% w/w or w/v. It may be present at about 0.02% w/v. Each component may, independently, be present in suspension, solution or emulsion. The preparation may be an herbal preparation, and may be a sports drink.

In another embodiment the preparation comprises:
Saponins (e.g. ginsenosides derived from Ginseng), and
(−) Schisandrin B.

The total saponins may be present between about 5 and about 30%, or between about 15 and about 20% w/w, w/v or v/v. Schisandrin B may be present between about 15 and about 40%, or between about 25 and about 30% w/w or w/v. Each component may or may not, independently, be present in suspension, solution or emulsion. Alternatively the preparation may have no added components other than saponins and Schisandrin B. It may consist only of (−) Schisandrin B and saponins. The ratio of (−) Schisandrin B to saponins may be between about 1:5 and 5:1. The preparation may be a solid. It may be a powder, and may be a powdered preparation. The preparation may be a pharmaceutical preparation.

In a second aspect of the invention there is provided a process for making a preparation for treatment or prevention of a condition in a patient comprising extracting plant matter containing Schisandrin B with a solvent to produce an extract. The plant matter may comprise one or more of leaves, flowers, seeds, stems, stalks, roots, fruit or other parts of a plant, or a combination of these. The plant matter may be dried before the extracting, and may be powdered. The plant may be any plant species which comprises Schisandrin B, for example a *Schisandra* plant, such as *Schisandra chinensis* (Fructus schisandrae). The step of extracting may comprise any of the known solvent extraction processes, including washing, boiling, refluxing, Soxhlet extraction, supercritical fluid extraction etc., or a combination of such methods. The washing may be at a convenient temperature up to the boiling point of the solvent, providing that it is not at a sufficient temperature and/or time to degrade the Schisandrin B. The solvent may be aqueous or organic. The solvent may be a supercritical fluid, such as supercritical carbon dioxide.

The extract may be the preparation, or the extract may be combined with one or more other components, for example liquids to produce the preparation. If the extracting comprises supercritical fluid extraction, the extraction process may produce a solid or powder extract, which may then be dissolved or suspended in a solvent, for example water or an alcohol (e.g. ethanol), or the extract may be taken up directly in the solvent. The solvent may have other matter, for example salts, electrolytes, nutrients, nutraceuticals, pharmaceuticals, drugs or other matter, dissolved therein. The extract, or the solution or suspension of the extract may be combined with a liquid to produce the preparation. The liquid may be a plant extract, or may contain a plant extract, or may be a solution or suspension of some other matter as described above. The preparation may be a solution, a suspension, and emulsion or a dispersion. Schisandrin B may be dissolved, suspended, dispersed or emulsified in the preparation. The process may comprise adding one or more of salts, electrolytes, nutrients, nutraceuticals, pharmaceuticals, drugs or other matter to the solvent. Alternatively the preparation may be a solid, or a powder.

In an embodiment the process comprises:

extracting a first plant material into a first solvent to generate a first extract, extracting *Schisandra chinensis* into a second solvent, and optionally removing (e.g. evaporating or vapourising) the second solvent, to generate a second extract, and combining the first and second extracts to form the preparation.

The first solvent may be organic, or may be aqueous, or may be partly organic and partly aqueous. It may comprise an alcohol. The first plant material may be a herb. It may comprise one or more of the leaves, stems, roots or other parts of a plant. The plant material may be dried, and may be powdered, before being extracted. The plant may be for example Ginseng. The first extract may comprise saponins, e.g. ginsenosides. The generation of the first extract may comprise at least partially removing the first solvent and dissolving, dispersing, suspending or emulsifying the residue in a third solvent. Third solvent may be aqueous, and may be water. The second solvent may be a supercritical fluid, e.g. supercritical carbon dioxide. The step of combining may comprise dissolving, dispersing, suspending or emulsifying the second extract in the first extract. The second extract may comprise Schisandrin B, and may comprise other lignans.

In a third aspect of the invention there is provided a process for making a preparation for treatment or prevention of a condition in a patient comprising combining Schisandrin B with at least one other component. At least one of the other components may be a liquid, or none of the other components may be a liquid. The Schisandrin B may be the (−) isomer. The liquid may be a solvent. It may be aqueous, and may be water. The liquid may comprise one or more of salts, electrolytes, nutrients, nutraceuticals, pharmaceuticals, drugs or other matter. The process may comprise isolating Schisandrin B prior to the combining. The process may comprise adding one or more of salts, electrolytes, nutrients, nutraceuticals, pharmaceuticals, drugs or other matter to the liquid, either before, during or after adding the Schisandrin B to the liquid. Each of the steps of adding may, independently, comprise dissolving, suspending, dispersing or emulsifying. Each may comprise agitating the liquid, for example swirling, stirring, shaking or sonicating. Each may comprise heating the liquid. The heating may be to a temperature below that required to denature or degrade the Schisandrin B, and optionally also below that required to denature or degrade other components of the preparation. The temperature may be between about 25 and 100° C.

The present invention also provides a preparation when made by one of the processes of the invention.

In a fourth aspect of the invention there is provided a method of treatment or prevention of a condition in a patient comprising administering to the patient a preparation according to the third aspect of the invention. The preparation may be administered in sufficient quantity over sufficient time to treat or prevent the condition. It may be administered between once per hour and once per week. The preparation may be administered as required. For example if the preparation is for the prevention of a cardiovascular condition following exercise, the preparation may be administered before, during and/or after exercise. The patient may drink or otherwise consume the preparation. The patient may be human or non-human, and may be a vertebrate. The vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, sheep, dog, cat, goat, llama, rabbit and a camel, for example.

In a fifth aspect of the invention there is provided a method of enhancing sports activities in a subject comprising administering to the subject a preparation comprising Schisandrin B. The Schisandrin B may be the (−) isomer. The preparation may be a preparation according to the present invention, as described above.

In a sixth aspect of the invention there is provided a method of treatment or prevention of a condition selected from the group consisting of a heart condition, a liver condition, a kidney condition, a lung condition, a cardiovascular condition, myocardial damage or infarction, coronary heart disease, impaired heart-lung function, cancer, heart failure, ischaemia, viral myocarditis, septic/hemorrhagic shock, liver failure, chronic hepatitis, chronic bronchitis, gastritis, type II diabetes, toxic side effects arising from cancer chemotherapy, aging and age-related diseases, liver failure, heart failure, Alzheimer's disease, Parkinson's disease, dehydration, failure of organs and muscle damage comprising administering to a subject in need thereof an effective amount of a pharmaceutical preparation comprising saponins and (−) Schisandrin B. The pharmaceutical preparation may be in the form of a powder. The method may comprise providing the pharmaceutical preparation to the subject. The subject may be a vertebrate, and the vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, cow, bull, ox, buffalo, sheep, dog, cat, goat, llama, rabbit, ape, monkey and a camel, for example. The administration may be oral administration, or it may be by inhalation. If the administration is by inhalation, the pharmaceutical preparation may be provided in an inhaler, and the step of providing the pharmaceutical preparation to the subject may comprise providing the inhaler having the preparation therein to the subject.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Schisandrin B may be isolated using a process comprising:
extracting plant matter containing Schisandrin B with a solvent to produce an extract; and
purifying the extract to isolate Schisandrin B.

The plant matter may comprise one or more of leaves, flowers, seeds, stems, stalks, roots, fruit or other parts of a plant, or a combination of these. The plant matter may be dried before the extracting, and may be powdered. The plant may be any plant species which comprises Schisandrin B, for example a *Schisandra* plant, such as *Schisandra chinensis* (*Fructus schisandrae*). The step of extracting may comprise any of the known solvent extraction processes, including washing, boiling, refluxing, Soxhlet extraction, supercritical fluid extraction etc., or a combination of such methods. The washing may be at a convenient temperature up to is the boiling point of the solvent, providing that it is not at a sufficient temperature and/or time to degrade the Schisandrin B. The solvent may be aqueous or organic. The solvent may be a supercritical fluid, such as supercritical carbon dioxide. The step of purifying may comprise any of the known methods for doing so, including column chromatography, preparative HPLC (normal phase or reverse phase), preparative GC, preparative GPC, recrystallisation or a combination of these.

The process may also comprise resolving of Schisandrin B into (+)Schisandrin B and (−)Schisandrin B. The resolution may comprise fractional crystallisation, chiral chromatography or some other suitable method.

The Schisandrin B isolated by the above process may be a mixture of isomers, or may be a single isomer. The single isomer may be (+)Schisandrin B or (−)Schisandrin B.

The inventors have demonstrated the antioxidant properties of SMS, of which *Schisandra* is the antioxidant determinant herb. In studies examining the effect of *Schisandra* on physical performance in thoroughbred horses, it was found that *Schisandra* could improve the heart-lung function as well as physical performance during running exercise. Serum lactic acid was reduced and the serum glucose was increased in *Schisandra* -treated horses. In addition, muscle damage in poorly performing horses appeared to be reversed with *Schisandra* treatment. Recently the present inventors have discovered the protective effect of a lignan-enriched extract of *Schisandra* on physical exercise-induced muscle damage and free radical-induced myocardial damage in rats.

While ginsenosides from Ginseng have long known for their cardioprotective effects, recent studies by the inventor have shown that schisandrin B, a dibenzocyclooctadiene derivative isolated from *Schisandra* , plays a pivotal role in protecting the ischemic heart by enhancing the mitochondrial glutathione antioxidant status and heat shock protein expression.

Results obtained from recent clinical studies indicated that SMS could improve clinical symptoms in patients suffering from coronary heart disease, viral myocarditis, septic/hemorrhagic shock as well as respiratory disorders. In combination with other herbs, contemporary clinical applications of SMS involve the treatment of chronic bronchitis, gastritis, type II diabetes and management of toxic side effects arising from cancer chemotherapy.

The inventors have also demonstrated the generalized organ protection (liver, heart, brain and skeletal muscle) afforded by SMS and *Schisandra* -derived lignans. *Schisandra* -derived lignans were found to be the activity determinant herb in the formula. Over the past few decades, the pharmacological activities of *Schisandra* or its lignan components have been extensively studied. Early evidence indicated that *Schisandra* could enhance heart-lung function and the body resistance to non-specific stimuli. *Schisandra* -derived lignans were found to produce beneficial effect on liver functions, particularly in enhancing the detoxification of xenobiotics and the regeneration of liver. Later studies also demonstrated their central nervous system modulating effect, anti-carcinogenic activity as well as cardioprotective action. The abilities of *Schisandra* -derived lignans to increase body resistance and suppress hepatocarcinogenesis and HIV infection illustrate much of their Qi-invigorating action in defending the body against exogenous challenges. The ability of *Schisandra* -derived lignans (such as Schisandrin B) to enhance mitochondrial glutathione antioxidant status and stimulate ATP generation represents an unique molecular mechanism involved in organ protection. Given the mitochondrial decay in aging, the ability of *Schisandra* -derived lignans/Schisandrin B to maintain mitochondrial functional integrity may retard the aging process and delay the onset of age-related diseases such as liver and heart failure, Alzheimer's disease, and Parkinson's disease. The inventors have described the use of Schisandrin B in protecting against liver toxicity in Chiu, P. Y, Tang M. H., Mak D. H. F., Poon M. K. T. and Ko K. M., "Hepatoprotective mechanism of schisandrin B: Role of mitochondrial glutathione antioxidant status and heat shock proteins", *Free Radical Biology & Medicine* Vol. 35, No. 4, pp. 368-380 (2003), the contents of which are incorporated herein by cross-reference.

Accordingly the inventors have designed an SMS-based and *Schisandra* lignan-enriched herbal preparation for generalized organ protection having the following composition.
saponins, and for example 0.6-1.5%
Lignans (e.g. derived from *Schisandra* ) for example 0.1-0.2%,
wherein the lignans include Schisandrin B for example 0.02-0.04%

Saponins are a class of plant glycosides, and those derived from Ginseng are designated ginsenosides. The herbal preparation may comprise up to about 3% saponins, or may have up to 2, 1.5, 1 or 0.5% saponins, or between about 0 and about 3%, or between about 0 and 2, 0 and 1.5, 0 and 1, 0 and 0.5, 0.5 and 3, 0.5 and 2, 1 and 3, 1 and 2, 0.5 and 1.5, 0.6 and 1.5, 0.3 and 1, 0.4 and 0.8, 0.5 and 0.7, or 0.5 and 1% saponins, and may have about 0.1, 0.2, 0.3, 0.4, 0.45, 0.5, 0.55, 0.6, 0.65, 0.7, 0.75, 0.8, 0.9, 1, 1.1, 1.2, 1.3, 1.4, 1.5, 1.6, 1.7, 1.7, 1.8, 1.9, 2, 2.5 or 3% saponins w/w or w/v. It may comprise up to about 0.5% lignans, or up to about 0.4, 0.3, 0.2 or 0.1% lignans, or between about 0.05 and about 0.5%, or between about 0.05 and 0.4, 0.05 and 0.25, 0.05 and 0.15, 0.07 and 0.13, 0.08 and 0.12, 0.09 and 0.11, 0.1 and 0.4, 0.1 and 0.3, 0.1 and 0.2, 0.2 and 0.5 or 0.2 and 0.4% lignans, and may comprise about 0.05, 0.06, 0.07, 0.08, 0.09, 0.1, 0.11, 0.12, 0.13, 0.14, 0.15, 0.2, 0.25, 0.3, 0.35, 0.4 or 0.5% lignans w/w or w/v. It may comprise up to about 0.1% Schisandrin B, or up to about 0.08, 0.05, 0.04 or 0.03% Schisandrin B, or between about 0.01 and abut 0.1%, or between about 0.01 and 0.05, 0.01 and 0.04, 0.01 and 0.03, 0.015 and 0.025, 0.018 and 0.022, 0.019 and 0.021, 0.02 and 0.1, 0.02 and 0.5, 0.02 and 0.04%, and may comprise about 0.01, 0.015, 0.016, 0.017, 0.018, 0.019, 0.02, 0.021, 0.022, 0.023, 0.024, 0.025, 0.03, 0.035, 0.04, 0.045, 0.05, 0.06, 0.07, 0.08, 0.09 or 0.1% Schisandrin B or may comprise more than 0.1% Schisandrin B. The Schisandrin B may be the (−) isomer. An example of a herbal preparation as described above comprises:
saponins, and about 0.6%
Lignans (e.g. derived from *Schisandra*) about 0.1%, wherein the lignans include Schisandrin B about 0.02%

The herbal preparation may be aqueous. The saponins may be ginsenosides.

An SMS-based pharmaceutical preparation with the following composition for the prevention and treatment of coronary heart disease was also designed.
Total saponins for example 15-20%
(−) Schisandrin B for example 25-30%

The saponins may comprise ginsenosides. Ginsenosides are steroid-like compounds, triterpene saponins, found exclusively in Panax species. The total saponins may be between about 5 and about 30%, or between about 5 and 25, 5 and 20, 5 and 15, 10 and 30, 15 and 30, 20 and 30, 15 and 25 or 15 and 20% w/w or w/v, and may be about 5, 10, 15, 16, 17, 18, 19, 20, 25 or 30% w/w or w/v. The amount of (−) Schisandrin B may be between about 15 and about 40%, or between about 15 and 35, 15 and 30, 15 and 25, 20 and 40, 25 and 40, 25 and 35, 25 and 30 or 20 and w/v, and may be about 15, 20, 25, 26, 27, 28, 29, 30, 35 or 40% w/w or w/v.

Each of the above preparations may be aqueous. They may additionally comprise well commonly used electrolytes and/or other excipients e.g. herbal extracts, fluids, solvents, antioxidants, preservatives, salts, nutrients, nutraceuticals, pharmaceuticals, drugs, pH control agents etc.

The preparation may have no added components other than saponins and Schisandrin B. It may consist only of (−) Schisandrin B and saponins. The ratio of (−) Schisandrin B to saponins may be between about 1:5 and about 5:1, or between about 1:5 and 2:1, 1:5 and 1:1, 1:5 and 1:2, 1:5 and 1:3, 1:2 and 5:1, 1:1 and 5:1, 2:1 and 5:1, 3:1 and 5:1, 1:4 ad 4:1, 1:3 and 3:1, 1:2 and 2:1, 1:1.5 and 1.5:1 or 2:1 and 1.25:1, or may be greater than about 5:1 or less than about 1:5 and may be about 1:5, 1:4, 1:3, 1:2, 1:1.5, 1:1.25, 1:1, 1.25:1, 1.5:1, 2:1, 3:1, 4:1 or 5:1 or may be some other ratio. The preparation may be a solid. It may be a powder, and may be a powdered preparation. It may be a paste.

A process for preparing a preparation according to the present invention comprises:

preparing a saponin-containing extract;
preparing a lignan-containing extract, which also contains Schisandrin B; and
combining the saponin-containing extract and the lignan-containing extract.

The saponin-containing extract may be a ginsenoside-containing extract. It may be prepared by extracting appropriate plant material with a solvent. The plant material may comprise one or more herbs, or part thereof, optionally dried and/or powdered. Suitable herbs include *Panax ginseng* and *Ophiopogon japonica*. The solvent may be aqueous, and may be acidic. It may be acidified with a suitable acid to a weakly acidic pH. The extraction may comprise boiling the solvent with the plant material therein, or it may comprise extracting the plant material with the solvent using a Soxhlet apparatus, or it may use some other method. This extraction may produce an initial extract, which may be used as the saponin-containing extract or may be treated further as described below.

Unwanted material may, if required, be removed from the initial extract by precipitation with ethanol followed by filtration, concentration and redissolution. Thus the initial extract, after filtration, may be concentrated by evaporation of at least part of the solvent before the precipitation with ethanol. The filtrate may be concentrated by evaporation of at least part of the solvent, and may be concentrated to a paste. It may then be dissolved in water to produce the saponin-containing extract.

The lignan-containing extract may be produced by extraction of herbal material from *Schisandra chinensis*, or a part thereof. The herbal material may be dried and/or powdered before the extraction. The extraction may use supercritical fluid extraction, or may employ solvent extraction, for example into an alcoholic solvent. Solvent extraction may be into methanol or ethanol, although if the preparation is to be consumed by or administered to a subject, particularly a human subject, ethanol may be preferred. Similarly, if supercritical fluid extraction is used, the extract may be taken up into a solvent, such as an alcohol. Again, methanol and ethanol are suitable solvents, however if the preparation is to be consumed by or administered to a subject, particularly a human subject, ethanol may be preferred.

The saponin-containing extract and the lignan-containing extract may be combined in a ratio appropriate to produce a preparation with the required amounts of saponins, lignans and (−) Schisandrin B. The ratio may be between about 10:1 and 15:1, or some other appropriate ratio. The combined extracts may then be pH adjusted to about neutral pH. This may use an acid, a base or a buffer, as appropriate.

Schisandrin B may be extracted from *Schisandra chinensis* using solvent extraction (e.g. Soxhlet or repeated extraction) into a liquid solvent, e.g., water or an aqueous solution, or an alcohol such as ethanol, methanol, isopropanol, or some other suitable solvents. This may be conducted at reflux temperature or at room temperature, or at some other temperature, depending on the nature of the solvent, and may be for example between about 10 and 100° C., or between about 20 and 100, 40 and 100, 60 and 100, 10 and 80, 40 and 80, 10 and 30, 10 and 20 or 30 and 50° C., and may be at about 10, 20, 30, 40, 50, 60, 70, 80, 90 or 100° C.

Alternatively it may be extracted into a supercritical fluid, for example supercritical carbon dioxide. The temperature may be greater than about 30° C., or greater than about 40, 50, 60, 70 or 80° C., or may be between about 30 and about 100, or between about 40 and 100, 60 and 100, 30 and 60, 40 and 60, 50 and 70, 55 and 65 or 58 and 72° C., and may be about 30, 40, 50, 55, 60, 65, 70, 75, 80, 90 or 100° C. The pressure may be greater than about 10 MPa, or greater than about 20, 30, 40, 50, 60, 70 or 80 MPa, or may be between about 10 and about 80 MPa, or between about 10 and 70, 10 and 50, 10 and 30, 30 and 80, 50 and 80, 20 and 70, 30 and 60, 40 and 60, 45 and 55 or 50 and 55 MPa, or may be about 10, 20, 30, 40, 45, 50, 55, 60, 65, 70 or 80 MPa, or may be greater than 80 MPa. It may be for example about 7500 psi (about 52 MPa). The restrictor may be kept at between about 50 and 100° C., or between about 60 and 100, 80 and 100, 50 and 70, 70 and 90 or 75 and 85° C., and may be kept at about 50, 60, 70, 80, 90 or 100° C. The flow rate may be between about 1 and about 10 ml/min, or between about 1 and 5, 1 and 2, 2 and 10, 5 and 10, 1 and 3, 1.5 and 2.5 or 1.8 and 2.2 ml/min. The dynamic extraction may be maintained for at least about 10 minutes, or at least about 15, 20, 25, 30, 34, 40 or 45 minutes, or between about 10 and about 40 minutes, or between about 10 and 30, 10 and 20, 20 and 40, 30 and 40, 25 and 35 or 28 and 32 minutes, and may be maintained for about 10, 15, 20, 25, 30, 34 or 40 minutes or longer. The extract may be collected in a solvent, for example water or an alcohol such as ethanol, methanol or isopropanol to produce a Schisandrin extract.

The extract, optionally in the solvent, may be combined with a second herbal extract, e.g. a saponin-containing extract. Thus an herb (e.g. *Panax ginseng* and/or *Ophiopogon japonica*) or part thereof, optionally powdered, optionally dried, may be extracted by a suitable solvent, e.g. an alcohol (ethanol, methanol, isopropanol etc.) or water. The solvent may be pH adjusted to an acidic pH, e.g. between about 2 and about 7, or between about 3 and 7, 4 and 7, 2 and 5, 3 and 6, 3 and 5, 2 and 4, 2.5 and 3.5 or 3 and 3.5. This may be achieved by addition of a suitable acid e.g. citric acid. The extraction may be at any temperature up to the boiling point of the solvent, and, depending on the solvent, may be for example greater than about 30° C., or greater than about 40, 50, 60, 70 or 80° C., or may be between about 30 and about 100, or between about 40 and 100, 60 and 100, 30 and 60, 40 and 60, 50 and 70, 90 and 100 or 95 and 100° C., and may be about 30, 40, 50, 55, 60, 65, 70, 75, 80, 90 or 100° C. The extraction may be for at least about 0.5 hours, or at least about 1, 1.5, 2, 2.5, 3, 4 or 5 hours, or for between about 0.5 and about 5 hours, or between about 1 and 5, 2 and 5, 3 and 5, 0.5 and 3, 0.5 and 1, 1 and 3, 1.5 and 2.5 or 1.8 and 2.2 hours, and may be for about 0.5, 1, 1.5, 1.6, 1.7, 1.8, 1.9, 2, 2.1, 2.2, 2.3, 2.4, 2.5, 3, 3.5, 4, 4.5 or 5 hours or longer. The extraction may be performed once, or more than once, e.g. 2, 3, 4 or 5 times or more than 5 times. The extract may be reduced in volume by evaporation, optionally at elevated temperature and/or reduced pressure (e.g. in a rotary evaporator), to between about 0.1 and about 0.5 of its volume, or between about 0.1 and 0.3 or 0.3 and 0.5, or 0.2 and 0.4 or 0.3 and 0.4 of its volume, or to about 0.1, 0.2, 0.25, 0.3, 0.33, 0.35, 0.4, 0.45 or 0.5 of its volume. The extract may be treated with a second fluid e.g. ethanol or isopropanol, in order to precipitate undesirable materials, which may be removed by filtration, centrifugation or other suitable process to isolate a liquid portion. The liquid portion may then be evaporated to a paste, optionally at elevated temperature and/or reduced pressure (e.g. in a rotary evaporator) and redissolved or resuspended in a suitable liquid, e.g. water to provide the second herbal extract.

The ratio of the second herbal extract to the Schisandrin extract may be between about 20:1 and about 1:1, or between about 20:1 and 5:1, 20:1 and 10:1, 20:1 and 15:1, 15:1 and 1:1, 10:1 and 1:1, 15:1 and 5:1, 15:1 and 10:1, 12:1 and 10:1 or 12:1 and 11:1, and may be about 20:1, 18:1, 16:1, 14:1, 13:1, 12:1, 11.5:1, 11:1, 10.5:1, 10:1, 8:1, 6:1, 4:1, 3:1, 2:1 or 1:1, and may be for example about 750:67, on a w/w or v/v basis. The combination of second herbal extract and Schisandrin extract may be adjusted to a pH between about 6 and 8, or between about 6.5 and 8, 7 and 8, 7 and 7.5, 6.5 and 7.5, 6.8 and 7.2, 6 and 7.5 or 6 and 7, and may be adjusted to a pH about 6, 6.5, 6.6, 6.7, 6.8, 6.9, 7, 7.1, 7.2, 7.3, 7.4, 7.5 or 8. The adjusting may use a strong acid, for example hydrochloric acid, which may be dilute, for example between about 0.1 and about 2M, or between about 0.1 and 1, 0,1 and 0.5, 0.5 and 1 or 1 and 2M, or may be about 0.1, 0.2, 0.3, 0.4, 0.5, 0.6, 0.7, 0.8, 0.9, 1, 1.5 or 2M. Alternatively the pH adjustment may use a buffer, e.g. a phosphate based buffer to achieve the desired pH. If the combination of second herbal extract and Schisandrin extract is acidic, the pH may be adjusted using base, e.g. dilute sodium hydroxide solution. The pH adjusted combination may be used as the preparation of the invention.

*Schisandra* fruit is has been used as a tonic herb in Chinese medicine. It has been used for the treatment of chronic hepatitis. Schisandrin B, the most abundant dibenzocyclooctadiene derivative, has been found to be a cardio-protective principle. Recent studies by the inventors have discovered that the enantiomers of schisandrin B ((+) Sch B and (−) Sch B) produce differential cardio-protective effect by enhancing the mitochondrial glutathione antioxidant status and heat shock protein expression. There is therefore disclosed the use of (−) Sch B as a pharmacological agent for the prevention and treatment of coronary heart disease. (our present invention is mainly related to heart protection) The inventors have found that (−) Schisandrin B is superior to (+) Schisandrin B in terms of efficacy, with respect to cardio-protection, and toxicity. Use of (−) Schisandrin B as an active nutraceutical/pharmacological ingredient may therefore be beneficial.

EXAMPLES

Example 1

Extraction and Purification of (−)Schisandrin B (Sch B)

Figure 1:
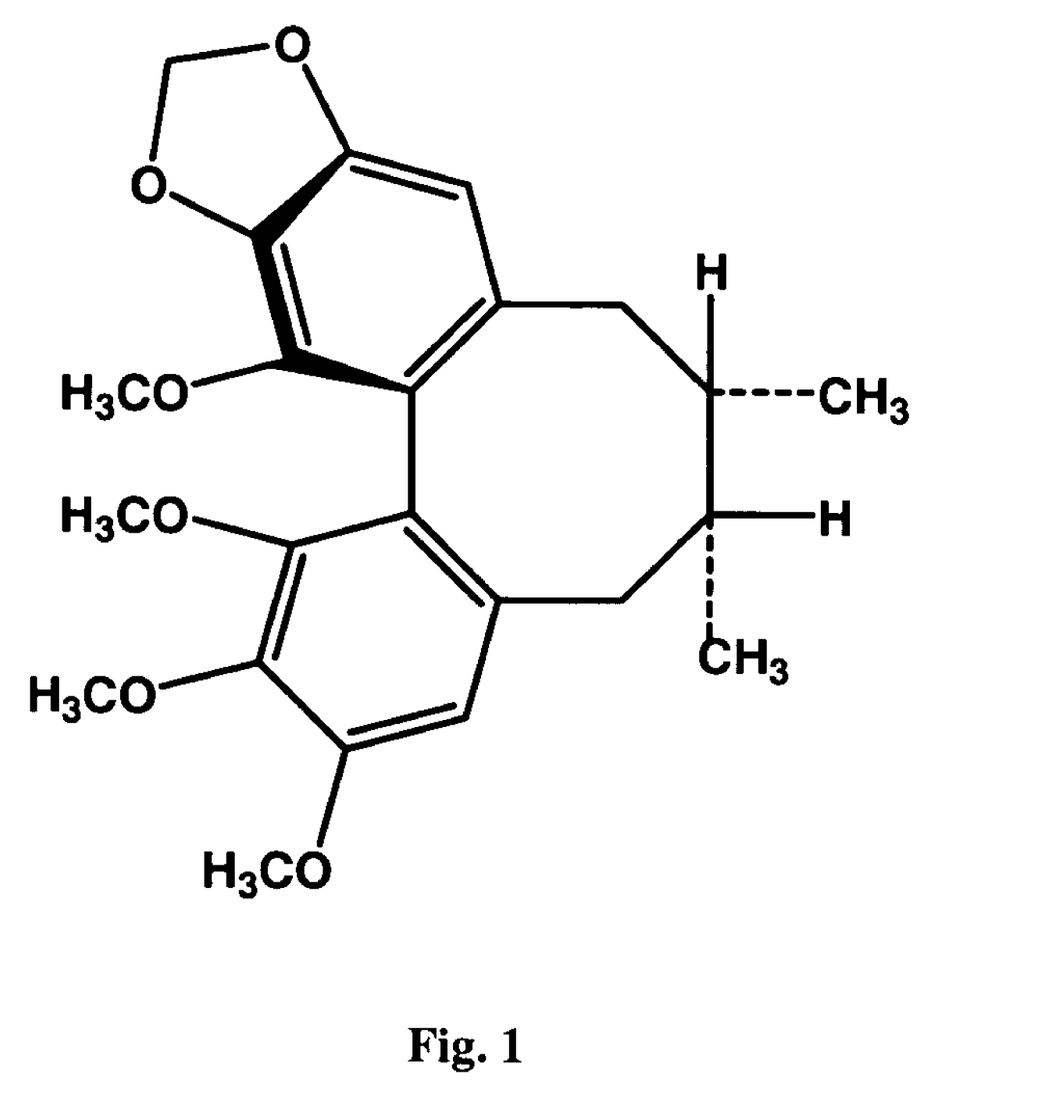
FIG. 1 shows the structure of (−)Schisandrin B.

Dried powder of the *Schisandra* fruits (*Schisandra chinensis* (Turcz) Baillon) was extracted with petroleum ether. The petroleum ether extract was then subjected to silica gel column chromatography using isocratic elution with acetone:petroleum ether (5:95, v/v). The Schisandrin B-containing fractions, as detected by thin layer chromatography, were pooled, and a crude crystalline fraction was obtained. The crystalline fraction was further purified by preparative reverse-phase HPLC using Prep Nova-Pak HR $C_{18}$ (19×300 mm) column eluted by methanol : $H_2O$ (75:25, v/v). Purified (−) Schisandrin B and (+) Schisandrin B were obtained, and the chirality of (−) Schisandrin B and (+) Schisandrin B (FIG. 1) was confirmed by optical rotation measurement, with the specific rotation measured in methanol at 20° C. being −47.2° and +55.3°, respectively. HPLC analysis using chiral column (CHIRACEL OD-H, 4.6×250 mm, Diacel Chemical Industrial Ltd.) revealed the purity of each enantiomer being higher than 95%.

Physical Properties:

$C_{23}H_{28}O_6$ MW: 400.48

Rhombic crystal (methanol), mp 117-119° C.

Example 2

Time-Course of (−) Schisandrin B-Induced Increase In Cellular GSH Level in H9c2 Cells: Protection Against Oxidative Challenge by Xanthine/Xanthine Oxidase (X/XO)

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 µg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Pretreatment and Xanthine/Xanthine Oxidase-Induced Cytotoxicity

Cultured H9c2 cells were treated with (−) Schisandrin B, (+) Schisandrin B or (±) Schisandrin B (dissolved in DMSO) at 6.25 µM (0.2% DMSO final concentration) for increasing periods of time. Control cells were given the vehicle (i.e. DMSO) only. Immediately following the drug or vehicle pretreatment, the cells were challenged with a mixture of xanthine (X) (0.1 mM) and xanthine oxidase (XO) (0.4 U/ml) for 4 h. The control cells were treated with the medium only. After the X/XO challenge, the medium was taken for the measurement of LDH activity, a biochemical index of cellular injury.

Measurement of Cellular GSH Level

The cells were washed twice with 0.5 ml cold phosphate-buffered saline (PBS), An aliquot (200 µl) of 3% sulfonsalicyclic acid was then added, and the mixture was incubate at 4° C. for 10 min. After centrifuging at 300 g for 15 min at 4° C., the supernatant was used for GSH measurement by an enzymatic method of Griffith (1980).

Results (−) Schisandrin B treatment at 6.25 µM caused a time-dependent increase in cellular reduced glutathione (GSH) in H9c2 cells, with the maximum stimulation occurring at 16 h post-dosing. The enhancing effect then gradually declined, with no detectable stimulatory effect at 48 h post-dosing (Table 1b).

(+) Schisandrin B or (±) Schisandrin B also produced a time-dependent increase in GSH level, with a smaller extent of stimulation than that of (−)Sch B at 16 h post-dosing (Table 1a). The beneficial effect of (−) Schisandrin B treatment became more evident after the oxidative challenged by X/XO. The (−) Schisandrin B-induced increase in GSH level was paralleled by the protection against cell injury induced by X/XO, as evidenced by the decrease in lactate dehydrogenase (LDH) leakage, with the maximum extent of protection occurring at 16 h post-dosing (TABLE1B).

(+) Schisandrin B or (±) Schisandrin B pretreatment also produced a time-dependent protection against X/XO-induced cellular injury, with a smaller degree of protection than that of (−) Schisandrin B at 16 h post-dosing (Table 1b).

TABLE 1a

| | GSH Level (nmol/mg protein) Time Post-Dosing (h) | | | | | |
|---|---|---|---|---|---|---|
| | 0 | 4 | 8 | 16 | 24 | 48 |
| Non-X/XO | | | | | | |
| (−) Sch B | 35.8 ± 1.04 | 46.8 ± 0.88 | 54.2 ± 1.42 | 92.6 ± 1.29*** (158%) | 79.0 ± 1.48 | 54.7 ± 3.58 |
| (+) Sch B | 34.2 ± 2.41 | 38.3 ± 1.48 | 46.3 ± 0.85 | 73.9 ± 1.38*** (117%) | 66.7 ± 1.83 | 59.0 ± 2.94 |
| (±) Sch B | 38.3 ± 1.16 | 44.1 ± 3.60 | 46.2 ± 1.90 | 85.8 ± 2.57*** (124%) | 76.6 ± 0.88 | 58.8 ± 6.54 |
| X/XO | | | | | | |
| (−) Sch B | 15.9 ± 0.45 | 18.3 ± 0.57 | 20.7 ± 0.61 | 25.1 ± 1.50** (57%)) | 17.8 ± 0.59 | 16.7 ± 0.63 |
| (+) Sch B | 13.9 ± 1.68 | 15.4 ± 0.55 | 16.8 ± 0.85 | 18.4 ± 0.33* (32%)) | 17.2 ± 0.36 | 14.1 ± 0.53 |
| (±) Sch B | 14.5 ± 1.06 | 15.8 ± 0.49 | 16.7 ± 1.32 | 22.3 ± 0.15** (54%) | 18.9 ± 0.50 | 14.3 ± 1.04 |

Drug was added at a final concentration of 6.25 µM. Xanthine (0.1 mM) and xanthine oxidase (0.4 U/ml) (X/XO) were added in challenged condition. Values given are mean ± S.E.M., with n = 3. The number in parentheses is the percent increase when compared with the respective unpretreated control (i.e. 0 h).
*$p < 0.05$,
**$p < 0.005$ and
***$p < 0.0005$, when compared with the respective control (i.e. 0 h).

TABLE 1b

| | LDH Leakage (U/L) Time Post-Dosing (h) | | | | | |
|---|---|---|---|---|---|---|
| | 0 | 4 | 8 | 16 | 24 | 48 |
| Non-X/XO | | | | | | |
| Control | 9.14 ± 0.49 | 8.64 ± 0.46 | 7.66 ± 0.51 | 8.32 ± 0.33 | 8.16 ± 0.24 | 8.86 ± 0.12 |
| X/XO | | | | | | |
| (−) Sch B | 34.8 ± 1.13 | 26.0 ± 0.92 | 22.0 ± 0.63 | 14.2 ± 0.35*** (*78%*) | 17.5 ± 0.85 | 26.3 ± 0.41 |
| (+) Sch B | 35.7 ± 0.24 | 31.3 ± 0.71 | 25.2 ± 0.45 | 19.4 ± 0.29*** (*62%*) | 22.4 ± 1.07 | 33.5 ± 0.17 |
| (±) Sch B | 33.9 ± 0.93 | 28.7 ± 1.35 | 22.8 ± 0.45 | 15.8 ± 0.91** (*65%*) | 20.1 ± 0.76 | 29.2 ± 0.57 |

Drug was added at a final concentration of 6.25 μM. Xanthine (0.1 mM) and xanthine oxidase (0.4 U/ml) (X/XO) were added in the challenged condition. Values given are mean ± S.E.M., with n = 3. The italicized number in parentheses is the percent protection when compared with the unpretreated control (i.e. 0 h).
**P < 0.005 and
***P < 0.0005 when compared with the respective control (i.e. 0 h), using Student's t test.

Example 3

Cytoprotective Effect of (−) Schisandrin B on Menadione-Induced Toxicity in H9c2

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Pretreatment and Menadione Challenge

Cultured H9c2 cells were treated with (−) Schisandrin B, (+) Schisandrin B or (±) Schisandrin B (dissolved in DMSO) at 6.25 μM (0.2% DMSO final concentration) for 16 h. Control cells were given the vehicle (i.e. DMSO) only. Immediately following the drug or vehicle pretreatment, the cells were challenged with menadione (dissolved in ethanol) at 12.5 μM (0.2% ethanol final concentration) for 4 h. The control cells were treated with the medium containing 0.2% ethanol only. After the menadione challenge, the medium was taken for the measurement of LDH activity, an biochemical index of cell injury.

Measurement of Cellular GSH Level

The cells were washed twice with 0.5 ml cold phosphate-buffered saline (PBS), An aliquot (200 μl) of 3% sulfonsalicyclic acid was then added, and the mixture was incubate at 4° C. for 10 min. After centrifuging at 300 g for 15 min at 4° C., the supernatant was used for GSH measurement by an enzymatic method of Griffith (1980).

Results (−) Schisandrin B treatment at 6.25 μM for 16 h increased cellular GSH level in H9c2 cells (Table 2). (+) Schisandrin B or (±) Schisandrin B treatment at the same dose also increased cellular GSH level, but to a smaller extent than that of (−) Schisandrin B (Table 2).

The beneficial effect of (−) Schisandrin B on H9c2 cells became more evident after the menadione challenge. (−) Schisandrin B pretreatment protected against the menadione cytotoxcity, as evidenced by the decrease in LDH leakage (Table 2). The cytoprotection was associated with an enhancement in cellular GSH level. Both (+) Schisandrin B and (+) Schisandrin B pretreatment protected against menadione cytotoxicity, but to a smaller degree than that of (−) Schisandrin B (Table 2).

TABLE 2

| | LDH (U/ml) | GSH Level (nmol/mg protein) |
|---|---|---|
| Non-Menadione | | |
| Control | 14.4 ± 0.40 | 34.7 ± 2.06 |
| (−) Sch B | 14.3 ± 0.29 | 64.0 ± 2.96*** (84%) |
| (+) Sch B | 13.5 ± 0.08 | 48.4 ± 0.60** (41%) |
| (±) Sch B | 14.6 ± 0.67 | 46.5 ± 2.58* (34%) |
| Menadione | | |
| Control | 30.2 ± 0.29 | 18.5 ± 0.47 |
| (−) Sch B | 20.6 ± 0.18*** (*60%*) | 33.3 ± 1.75** (81%) |
| (+) Sch B | 24.7 ± 0.56** (*30%*) | 24.5 ± 2.03* (55%) |
| (±) Sch B | 23.6 ± 0.56** (*43%*) | 28.9 ± 0.66*** (56%) |

The drug was added at a final concentration of 6.25 μM. Menadione was added at a final concentration of 12.5 μM for 4 h. Values given are mean ± S.E.M., with n = 3. The italicized number in parentheses is the percent protection when compared with the menadione control. The non-italicized number in parentheses is the percent increase when compared with the respective control (non-menadione or menadione),
*p < 0.05, p < 0.005 and p < 0.0005 when compared with the respective control, using Student's t test.

Example 4

Effect of (−) Schisandrin B on Hsp25 and Hsp70 Expression in H9c2 Cells

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Treatment

Cultured H9c2 cells were treated with (−) Schisandrin B, (+) Schisandrin B or (±)Schisandrin B (dissolved in DMSO) at 6.25 μM (0.2% DMSO final concentration) for increasing periods of time. Control cells were given the vehicle (i.e. DMSO) only.

Measurement of Heat Shock Protein Levels

Immediately following the drug treatment, the cells were washed twice with 0.5 ml cold PBS and treated with 100 μl lysis buffer containing 20 mM Tris HCl, 3 mM EGTA, 1% Triton X-100, 10% glycerol and 2 mM dithiothreitol, pH 7.5, with freshly added protease inhibitors (1 mM phenylmethylsulfonyl fluoride, 0.1 mM benzamide, 5 μg/ml leupeptin, 5 μg aproptinin and 5 μg/ml pepstain A). The mixture was incubated at 4° C. for 15 min with constant shaking. Then the cells were scraped off from the plate, and the extract was transferred to a microcentrifuge tube for centrifugation at 2,400 g for 3 min at 4° C. The resultant supernatant was used for Hsp analysis. Hsp25 and Hsp70 levels was estimated by Western blot analysis using specific antibodies (anti-Hsp25, catalog # SPA-801; anti-Hsp70, catalog # SPA-812) from StressGen (Vancouver, BC, Canada) following SDS-PAGE analysis cell lysates, using a separating gel of 10% acrylamide as described in Ip et. al. [2001]. Hsp25/27 and Hsp70 (human recombinant proteins from StressGen) and actin (bovine muscle from Sigma) were used as markers for reference. The immuno-stained protein bands were revealed by enhanced chemiluminescence reaction (Amersham ECL+) followed by the exposure to X-ray film. All immunoblots were analyzed by densitometry, and the amounts (arbitrary units) of Hsp were normalized with reference to actin levels (arbitrary units) in the sample.

Results (−) Schisandrin B treatment at 6.25 μM caused a time-dependent increase in Hsp25 and Hsp70 levels in H9c2 cells, with the maximum stimulation occurring at 24 h post-dosing and the extent of increase in Hsp7O being more prominent (Table 3a, b).

While both (+) Schisandrin B and (±) Schisandrin B could increase Hsp25 level to a similar extent as (−) Schisandrin B, the extent of stimulation afforded by (+) Schisandrin B or (±) Schisandrin B treatment in Hsp7O levels was much smaller than that of (−) Schisandrin B (Table 3a,b).

TABLE 3a

| | Hsp 25 Level (AU) Time Post-Dosing (h) | | | | |
|---|---|---|---|---|---|
| | 0 | 8 | 16 | 24 | 48 |
| (−) Sch B | 1722 ± 99 | 1386 ± 50 | 1432 ± 83 | 1956 ± 113 (14%) | 1878 ± 108 |
| (+) Sch B | 1722 ± 99 | 1832 ± 105 | 1498 ± 86 | 2168 ± 125** (26%) | 1673 ± 97 |
| (±) Sch B | 1413 ± 76 | 1512 ± 39 | 1611 ± 93 | 1728 ± 101** (24%) | 1332 ± 77 |

TABLE 3b

| | Hsp 70 Level (AU) Time Post-Dosing (h) | | | | |
|---|---|---|---|---|---|
| | 0 | 8 | 16 | 24 | 48 |
| (−) Sch B | 465 ± 14.3 | 486 ± 16.7 | 548 ± 6.67 | 1058 ± 61*** (128%) | 556 ± 32.1 |
| (+) Sch B | 465 ± 14.3 | 576 ± 20.3 | 657 ± 13.4 | 834 ± 48.1** (79%) | 656 ± 37.8 |
| (±) Sch B | 434 ± 15.5 | 389 ± 24.7 | 652 ± 23.9 | 639 ± 23.4** (47%) | 419 ± 15.4 |

Drug was added at a final concentration of 6.25 μM. Values given are mean ± S.E.M., with n = 3. The number in the parentheses is the percent increase when compared with the unpretreated control (i.e. 0 h).
**P < 0.005 and
***p < 0.0005 when compared with the respective control (i.e. 0 h), using Student's t test.

Example 5

Cytotoxicity Test on (−) Schisandrin B in H9c2 Cells

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 µg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Treatment

Cultured H9c2 cells were treated with (−) Schisandrin B or (+) Schisandrin B (dissolved in DMSO) at 6.25 FM (0.2% DMSO final concentration) at increasing concentrations or at increasing concentrations for 24 h. Control cells were given the vehicle (i.e. DMSO) only.

Cell Viability Measurement

Cell viability was evaluated by trypan blue staining (dead cells) and LDH leakage as well as WST staining (viable cells).

Figure 2A:
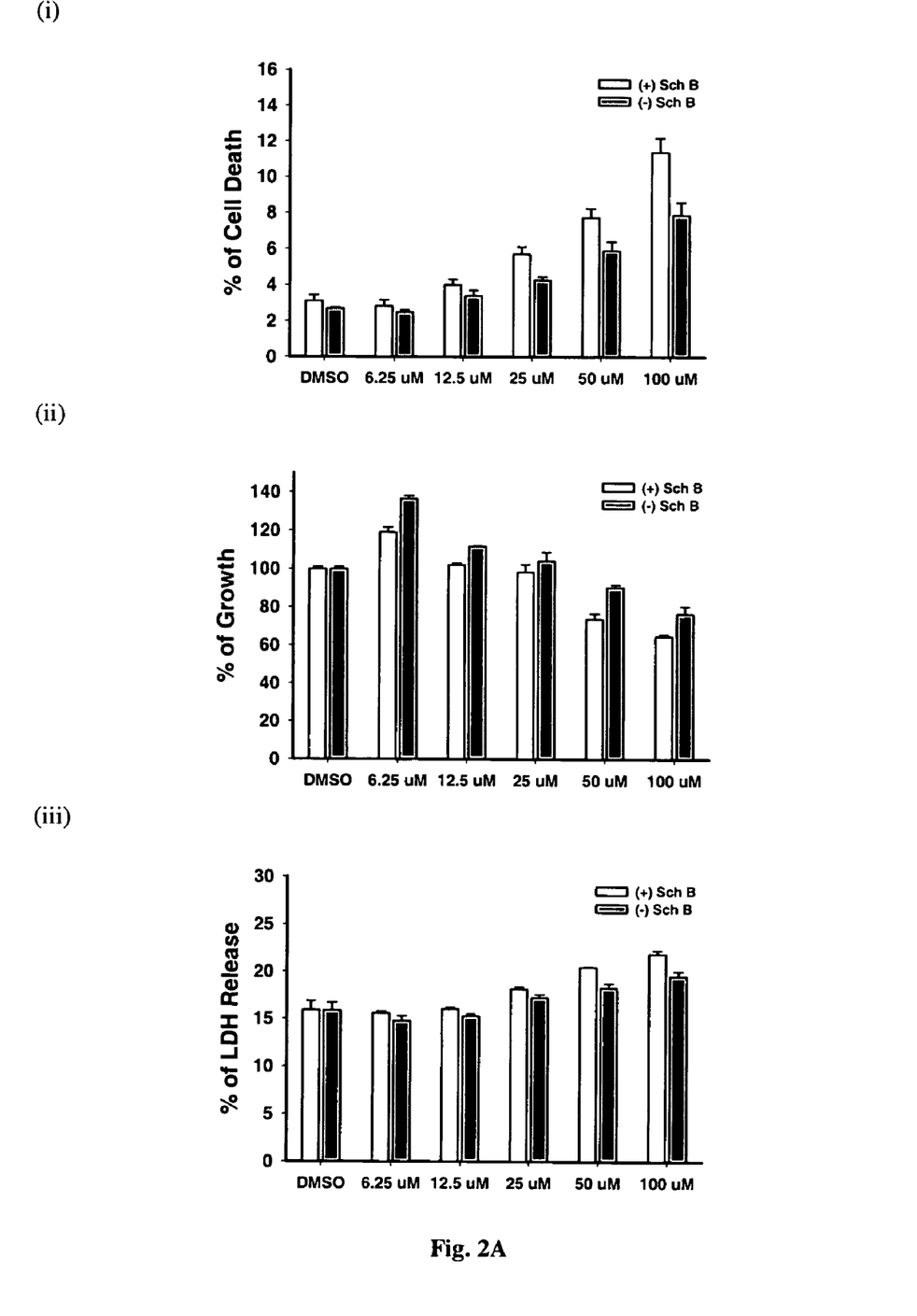
FIG. 2 shows graphs illustrating the cytotoxic effect of (−)Schisandrin B as a function of (A) dose, and (B) time;.
Figure 2B:
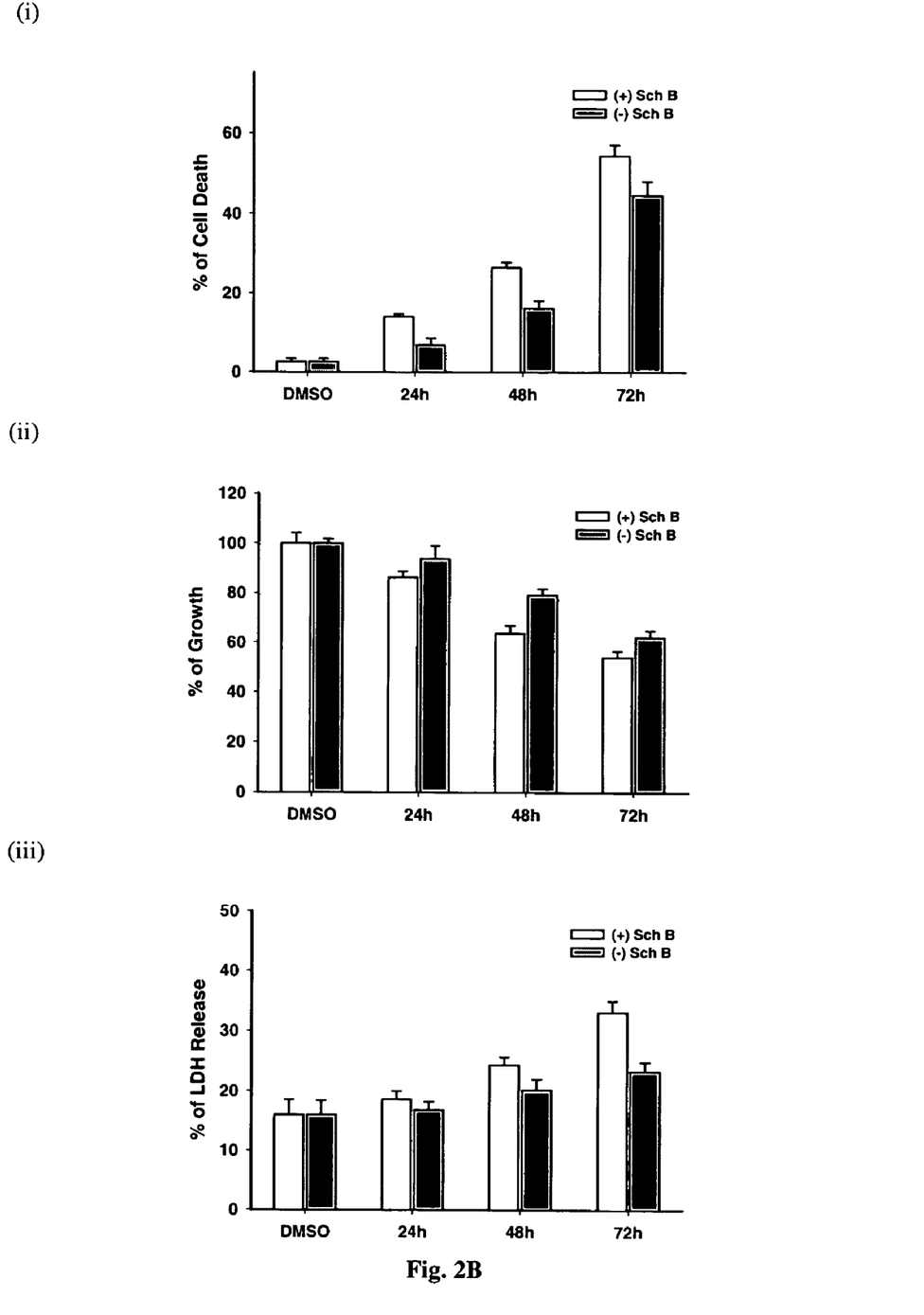

Results (+) Schisandrin B treatment also caused a dose-dependent cytotoxic effect, with the percentage of cell death being 11% at 100 µM (FIG. 2a). The differential cytotoxicity between (−) Schisandrin B and (+) Schisandrin B was confirmed by treating the cells with the drug at 100 µM for increasing periods of time up to 72 h. (−) Schisandrin B showed a lower toxicity, as assessed by the three parameters, than that of (+) Sch B (FIG. 2b). In FIG. 2b, values given are mean±S.E.M., with n=3.

Example 6

Effects of (−) Schisandrin B on Myocardial Mitochondria Functional Ability and Glutathione Antioxidant Status in Young Male and Female Rats: Protection Against Ischemia-Reperfusion Injury

Methods

Animal Pretreatment

Male/Female adult Sprague-Dawley rats (~10 weeks old) were maintained under a 12-h dark/light cycle at about 22° C. and allowed food and water ad libitum. Animals were randomly divided into groups, with at least 5 animals in each. In the pretreatment groups, rats were treated intragastrically with (−) Schisandrin B at a daily dose of 1 or 10 mg/kg for 35 days. Control animals received oil only (10 ml/kg). Twenty-four hours following the last dosing, hearts were isolated from control or drug-pretreated rats and then subjected to Langendorff perfusion as described below.

Isolated-Perfused Rat Heart

The heart was excised quickly and immediately immersed in ice-cold and heparinized (50 unit/ml) saline. The aorta was cannulated and then transferred to a warm and moistured chamber of the perfusion apparatus. The heart was retrogradely perfused according to Langendorff method as described (Yim and Ko 1999).

Myocardial Ischemia-Reperfusion (I-R)

After an initial 30-min of perfusion for equilibration, the isolated heart was subjected to a 40-min period of 'no-flow' global ischemia followed by 20 min. of reperfusion. Coronary effluent was collected in 1-min fractions at increasing time intervals during the course of equilibration and reperfusion. The fractions were immediately put on ice until assay for lactate dehydrogenase (LDH) activity. The extent of LDH leakage during the reperfusion period, an indirect index of myocardial injury, was estimated by computing the area under the curve of the graph plotting the percent LDH activity (with respect to the mean pre-ischemic value measured during the equilibration period) against the reperfusion time (1-20 min), as described (Yim and Ko 1999). Immediately after the I-R procedure, heart ventricular tissue samples were obtained for biochemical analysis.

Preparation of Mitochondrial Fractions

Myocardial tissue samples were rinsed with ice-cold isotonic buffer (50 mM Tris, 0.32 M sucrose, 1 mM $Na_2EDTA$, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 µl of 2 mg/ml soybean trypsin inhibitor and constituted the mitochondrial fractions.

Biochemical Analysis

Myocardial mitochondrial ATP generation capacity was measured by incubating 200 µl of nucleus-free tissue homogenate with 200 µl of substrate solution (containing 100 mM glutamate and 34 mM malate) and 20 µl ADP (2.3 mM) for 10 min at 37° C., and the ATP level were measured using an assay kit from Sigma Chemical Co. (St. Louis, Mo., USA). LDH activity was spectrophotometrically measured as described (Yim and Ko 1999).

Aliquots (500 µl) of mitochondrial fractions were taken for measuring mitochondrial GSH level by HPLC methods, using GSH as standards, respectively, as described (Chiu et al 2002). Aliquots (400 µl) of mitochondrial fractions were mixed with 933 [t] Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Statistical Analysis

Data obtained from animal experiments were analyzed by one-way ANOVA followed by Duncan's multiple range test to detect the inter-group difference. Significant difference was determined when $p<0.05$.

Results

Chronic (−) Schisandrin B treatment caused an enhancement in myocardial functional status in both male and female rats, as evidenced by the dose-dependent increase in ATP generation, with the stimulatory effect on male rats being more prominent (Table 4a). (−) Schisandrin B treatment also enhanced the mitochondrial glutathione antioxidant status in male and female rats, as indicated by dose-dependent increases in GSH level and glutathione antioxidant enzyme activities, with the stimulatory effect being comparable between male and female rats (Table 4a).

The beneficial effect of (−) Schisandrin B treatment became more apparent after the I-R challenge. While the male hearts were more susceptible to I-R injury, (−) Schisandrin B pretreatment produced a dose-dependent protection against myocardial I-R injury, as evidenced by the decrease in the extent of LDH leakage, with the degree of protection being comparable between male and female rats (Table 4b).

TABLE 4a

| | Mitochondrial Functional Status ATP | Mitochondrial Glutathione Antioxidant Status | | | |
|---|---|---|---|---|---|
| | Generation ($\mu$mol/min/mg protein) | GSH (nmol/mg protein) | GPX (mU/mg Protein) | GRD (mU/mg protein) | GST (mU/mg protein) |
| Male | | | | | |
| Control (−) Sch B | 2.80 ± 0.75 | 11.6 ± 0.37 | 52.3 ± 1.07 | 5.35 ± 0.41 | 10.1 ± 0.61 |
| 1 mg/kg | 5.58 ± 0.19[a] (99%) | 18.1 ± 1.06[a] (56%) | 77.3 ± 3.78[a] (48%) | 6.76 ± 0.29 (26%) | 12.8 ± 0.10 (65%) |
| 10 mg/kg | 6.74 ± 0.37[a] (141%) | 23.8 ± 1.10[a] (105%) | 83.7 ± 2.12[a] (60%) | 7.59 ± 0.13[a] (42%) | 14.5 ± 0.36[a] (83%) |
| Female | | | | | |
| Control (−) Sch B | 3.25 ± 0.19 | 10.4 ± 0.41 | 51.1 ± 4.17 | 4.69 ± 0.15 | 11.1 ± 0.51 |
| 1 mg/kg | 4.11 ± 0.19[b] (26%) | 17.3 ± 1.11[b] (60%) | 73.2 ± 4.98[b] (43%) | 6.30 ± 0.37[b] (34%) | 14.1 ± 0.58[b] (37%) |
| 10 mg/kg | 5.79 ± 0.37[b] (78%) | 21.6 ± 0.38[b] (107%) | 78.3 ± 2.94[b] (53%) | 8.02 ± 0.55[b] (71%) | 16.9 ± 0.90[b] (63%) |

Animals were orally treated with (−) Sch B at the indicated daily dose for 35 days. Myocardial mitochondrial reduced glutathione (GSH) level and Se-glutathione peroxidase (GPX), glutathione reductase (GRD) and glutathione S-transferases (GST) activities were measured. Values given are mean ± S.E.M., with n = 5. The number in the parentheses is the percent increase when compared with the respective untreated control.
[a]significantly different from the male control;
[b]significantly different form the female control TABLE 4b

| | LDH Leakage (AU) |
|---|---|
| Non-I-R | |
| Male | |
| Control (−) Sch B | 832 ± 20.6 |
| 1 mg/kg | 804 ± 18.0 |
| 10 mg/kg | 820 ± 13.8 |
| Female | |
| Control (−) Sch B | 803 ± 8.15 |
| 1 mg/kg | 776 ± 22.1 |
| 10 mg/kg | 813 ± 14.0 |
| I-R | |
| Male | |
| Control | 5366 ± 349 (5.4-fold) |
| (−) Sch B | |
| 1 mg/kg | 3638 ± 125[a] (*37%*) |
| 10 mg/kg | 2775 ± 55.8[a] (*57%*) |
| Female | |
| Control | 3831 ± 127 (4.7-fold) |
| (−) Sch B | |
| 1 mg/kg | 2861 ± 70.6[b] (*31%*) |
| 10 mg/kg | 2023 ± 83.1[b] (*60%*) |

Values given are mean ± S.E.M., with n = 5. The non-italicized number in parentheses is the number of fold increase when compared with the respective control. The italicized number in parentheses is the percent protection when compared with the respectively unpretreated control.
[a]significantly different from the male control;
[b]significantly different form the female control

Example 7

Effects of (−) Schisandrin B on Myocardial Mtiochondrial Functional Ability and Glutathione Antioxidant Status in Old Male and Female Rats: Protection Against Ischemia-Reperfusion Injury Methods Aged male and female rats (~12 months old) were administered with liposome-encapsulated (−) Schisandrin B in drinking water for 35 days, with the daily dose estimated to be 10 mg/kg.

Animal Pretreatment

Male/Female adult Sprague-Dawley rats (~12 months old) were maintained under a 12-h dark/light cycle at about 22° C. and allowed food and water ad libitum. Animals were randomly divided into groups, with at least 5 animals in each. In the pretreatment groups, rats were treated with liposome-encapsulated (−) Schisandrin B in drinking water for 35 days, with the estimated daily dose of 10 mg/kg. Control animals received empty liposomes-containg drinking water. Twenty-four hours following the last dosing, hearts were isolated from control or drug-pretreated rats and then subjected to Langendorff perfusion as described below.

Isolated-Perfused Rat Heart

The heart was excised quickly and immediately immersed in ice-cold and heparinized (50 unit/ml) saline. The aorta was cannulated and then transferred to a warm and moistured chamber of the perfusion apparatus. The heart was retrogradely perfused according to Langendorff method as described (Yim and Ko 1999).

Myocardial Ischemia-Reperfusion (I-R)

After an initial 30-min of perfusion for equilibration, the isolated heart was subjected to a 40-min period of 'no-flow' global ischemia followed by 20 min of reperfusion. Coronary effluent was collected in 1-min fractions at increasing time intervals during the course of equilibration and reperfusion. The fractions were immediately put on ice until assay for lactate dehydrogenase (LDH) activity. The extent of LDH leakage during the reperfusion period, an indirect index of myocardial injury, was estimated by computing the area under the curve of the graph plotting the percent LDH activity (with respect to the mean pre-ischemic value measured during the equilibration period) against the reperfusion time (1-20 min), as described (Yim and Ko 1999). Immediately after the I-R procedure, heart ventricular tissue samples were obtained for biochemical analysis.

Preparation of Mitochondrial Fractions

Myocardial tissue samples were rinsed with ice-cold isotonic buffer (50 mM Tris, 0.32 M sucrose, 1 mM $Na_2EDTA$, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 µl of 2 mg/ml soybean trypsin inhibitor and constituted the mitochondrial fractions.

Biochemical Analysis

Myocardial mitochondrial ATP generation capacity was measured by incubating 200 µl of nucleus-free tissue homogenate with 200 RI of substrate solution (containing 100 mM glutamate and 34 mM malate) and 20 µl ADP (2.3 mM) for 10 min at 37° C., and the ATP level were measured using an assay kit from Sigma Chemical Co. (St. Louis, Mo., USA). LDH activity was spectrophotometrically measured as described (Yim and Ko 1999).

Aliquots (500 µl) of mitochondrial fractions were taken for measuring mitochondrial GSH level by HPLC methods, using GSH as standards, respectively, as described (Chiu et al 2002). Aliquots (400 µl) of mitochondrial fractions were mixed with 933 µl Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Statistical Analysis

Data obtained from animal experiments were analyzed by one-way ANOVA followed by Duncan's multiple range test to detect the inter-group difference. Significant difference was determined when $p<0.05$.

Results (−) Schisandrin B treatment enhanced the myocardial mitochondrial functional ability in old male and female rats, as evidenced by the increase in ATP generation, with the degree of stimulation being more prominent in female rats (Table 5a). (−) Schisandrin B treatment also enhanced the myocardial mitochondrial glutathione antioxidant status, as indicated by increases in GSH level and some of the glutathione antioxidant enzyme activities, with the stimulatory effect on male rats being more prominent (Table 5a).

While there were no apparent difference in the susceptibility to I-R injury between the hearts prepared from old male and female rats, (−) Schisandrin B pretreatment protected against I-R injury in old male and female hearts, as evidenced by the decrease in LDH leakage, with the degree of protection being comparable between male and female rats (Table 5b).

TABLE 5a

| | Mitochondrial Functional Status ATP | Mitochondrial Glutathione Antioxidant Status | | | |
|---|---|---|---|---|---|
| | Generation (µmol/min/mg protein) | GSH (nmol/mg protein) | GPX (mU/mg Protein) | GRD (mU/mg protein) | GST (mU/mg protein) |
| Male | | | | | |
| Control | 3.38 ± 0.10 | 3.52 ± 0.22 | 45.5 ± 2.04 | 2.67 ± 0.06 | 16.2 ± 0.26 |

TABLE 5a-continued

|  | Mitochondrial Functional Status ATP Generation (μmol/min/mg protein) | Mitochondrial Glutathione Antioxidant Status | | | |
|---|---|---|---|---|---|
|  |  | GSH (nmol/mg protein) | GPX (mU/mg Protein) | GRD (mU/mg protein) | GST (mU/mg protein) |
| (−) Sch B |  |  |  |  |  |
| 10 mg/kg | $3.75 \pm 0.06$ (11%) | $4.43 \pm 0.09^a$ (265%) | $52.2 \pm 0.72^a$ (15%) | $3.72 \pm 0.29^a$ (39%) | $17.5 \pm 0.76$ |
| Female |  |  |  |  |  |
| Control (−) Sch B | $3.00 \pm 0.24$ | $5.19 \pm 0.10$ | $46.8 \pm 3.62$ | $5.02 \pm 0.71$ | $11.2 \pm 1.00$ |
| 10 mg/kg | $4.43 \pm 0.10^b$ (48%) | $6.80 \pm 0.28^b$ (31%) | $44.6 \pm 4.29$ | $5.65 \pm 0.65$ (13%) | $14.0 \pm 0.45^b$ |

Animals were treated with (−) Sch B in drinking water at the indicated daily dose for 15 days. Myocardial mitochondrial reduced glutathione (GSH) level and Se-glutathione peroxidase (GPX), glutathione reductase (GRD) and glutathione S-transferases (GST) activities were measured. Values given are mean ± S.E.M., with n = 5. The number in the parentheses is the percent increase when compared with the respective untreated control.
[a]significantly different from the male control;
[b]significantly different from the female control TABLE 5b

|  | LDH Leakage (AU) |
|---|---|
| Non-I-R |  |
| Male |  |
| Control (−) Sch B | $645 \pm 98.0$ |
| 10 mg/kg | $570 \pm 66.8$ |
| Female |  |
| Control (−) Sch B | $782 \pm 21.3$ |
| 10 mg/kg | $611 \pm 49.7$ |
| I-R |  |
| Male |  |
| Control (−) Sch B | $5540 \pm 314$ (7.6-fold) |
| 10 mg/kg | $2426 \pm 219^a$ (*62%*) |
| Female |  |
| Control (−) Sch B | $6887 \pm 250$ (7.8-fold) |
| 10 mg/kg | $4534 \pm 86.5^b$ (*56%*) |

Values given are mean ± S.E.M., with n = 5. The non-italicized number in parentheses is the number of fold increase when compared with the respective control. The italicized number in parentheses is the percent protection when compared with the respective unpretreated control.
[a]significantly different from the male I-R control;
[b]significantly different from the female I-R control Example 8

Effects of Chronic (−) Schisandrin B Treatment on Mitochondrial Functional Ability and Antioxidant Status as Well as Tissue Heat Shock Protein Expression in Various Tissues in Young Female Rats Methods Drug Treatment Female Sprague-Dawley rats (8 weeks old) were maintained under a 12-h dark/light cycle at about 22° C. and allowed food and water ad libitum. Drug treated animals received a daily bolus dose of (−) Schisandrin B, (x-lipoic acid (α-LA) or α-tocopherol (α-Toc) at 10, 5 and 70 mg/kg, respectively, for 15 days. The dosages were determined with reference to the equivalent amount of crude herb prescribed for human or the daily recommended intake in health supplements. The control animals received olive oil only. Twenty-four hours after the last dose, the pentobarbital-anesthetized animals were sacrificed by cardiac excision, and brain heart, liver and skeletal muscle tissues were obtained.

Preparation of Mitochondrial Fractions

Tissue samples (brain, heart, liver, and skeletal muscle) were rinsed with ice-cold isotonic buffer (50 mM Tris, 0.32 M sucrose, 1 mM Na$_2$EDTA, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 μl of 2 mg/ml soybean trypsin inhibitor and constituted the mitochondrial fractions.

Biochemical Analysis

Mitochondrial ATP generation capacity was measured by incubating 200 µl of nucleus-free tissue homogenate with 200 µl of substrate solution (containing 100 mM glutamate and 34 mM malate) and 20 µl ADP (2.3 mM) for 10 min at 37° C., and the ATP level were measured using an assay kit from Sigma Chemical Co. (St. Louis, Mo., USA). Aliquots (500 µl) of mitochondrial fractions were taken for measuring mitochondrial GSH level by HPLC methods, using GSH as standards, respectively, as described (Chiu et al 2002). Aliquots (400 µl) of mitochondrial fractions were mixed with 933 µl Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Hsp25 and Hsp70 levels was estimated by Western blot analysis using specific antibodies (anti-Hsp25, catalog # SPA-801; anti-Hsp70, catalog # SPA-812) from StressGen (Vancouver, BC, Canada) following SDS-PAGE analysis of the nuclear-free tissue homogenates, using a separating gel of 10% acrylamide as described in Ip et. al. (2001). Hsp25/27 and Hsp70 (human recombinant proteins from StressGen) and actin (bovine muscle from Sigma) were used as markers for reference. The immuno-stained protein bands were revealed by alkaline phosphatase reaction. All immuno-blots were analyzed by densitometry, and the amounts (arbitrary units) of Hsp were normalized with reference to actin levels (arbitrary units) in the sample.

Results (−)Sch B treatment enhanced the mitochondrial functional status in brain, heart and liver tissue, as evidenced by the increase in ATP generation capacity (TABLE 6A). No detectable change in ATP generation was observed in skeletal muscle tissue (TABLE 6 A). (−) Schisandrin B treatment enhanced the mitochondrial antioxidant status in all tissues tested, as indicated by increases in GSH level and glutathione antioxidant enzyme activities as well as ct-tocopherol level (Table 6a).

Antioxidant treatment using α-LA or α-Toc also enhanced the mitochondrial antioxidant status in various tissues to varying degrees. However, both α-LA and α-Toc treatment decreased, in contrast to the enhancing effect of (−) Schisandrin B, the mitochondrial ATP generation capacity in various tissues.

(−) Schisandrin B treatment also increased the Hsp70 level in all tissues tested, with the extent of stimulation in brain tissue being more prominent. No detectable changes in Hsp25 level were observed in all tissues (Table 6b).

TABLE 6a

| | Mitochondrial Functional Status ATP generation | Mitochondrial Antioxidant Status | | | | |
|---|---|---|---|---|---|---|
| | | GSH | GRD | GPX | GST | α-Toc |
| Brain | | | | | | |
| Control | 100 ± 2 | 100 ± 5 | 100 ± 4 | 100 ± 6 | 100 ± 5 | 100 ± 3 |
| (−) Sch B | 143 ± 2** | 147 ± 4** | 150 ± 9*** | 163 ± 9** | 143 ± 4*** | 141 ± 7** |
| α-LA | 72 ± 4* | 93 ± 2 | 131 ± 5** | 126 ± 9* | 103 ± 3 | 110 ± 6 |
| α-Toc | 62 ± 8* | 119 ± 6* | 153 ± 10** | 121 ± 12 | 121 ± 5* | 139 ± 9* |
| Heart | | | | | | |
| Control | 100 ± 5 | 100 ± 10 | 100 ± 11 | 100 ± 6 | 100 ± 6 | 100 ± 3 |
| (−) Sch B | 131 ± 4** | 159 ± 2*** | 163 ± 6*** | 143 ± 7*** | 161 ± 5** | 160 ± 13*** |
| α-LA | 68 ± 9 | 103 ± 4 | 144 ± 11* | 105 ± 9 | 119 ± 6* | 111 ± 4* |
| α-Toc | 95 ± 12 | 152 ± 9* | 243 ± 20** | 130 ± 10* | 159 ± 7** | 151 ± 5** |
| Liver | | | | | | |
| Control | 100 ± 9 | 100 ± 10 | 100 ± 1 | 100 ± 8 | 100 ± 3 | 100 ± 13 |
| (−) Sch B | 134 ± 5* | 175 ± 5*** | 161 ± 10*** | 135 ± 3*** | 154 ± 4*** | 167 ± 14** |
| α-LA | 77 ± 5* | 117 ± 2 | 143 ± 8** | 159 ± 10** | 112 ± 3* | 124 ± 13 |
| α-Toc | 83 ± 8 | 133 ± 11 | 161 ± 5*** | 169 ± 14** | 128 ± 3* | 214 ± 31** |
| Skeletal Muscle | | | | | | |
| Control | 100 ± 24 | 100 ± 5 | 100 ± 6 | 100 ± 8 | 100 ± 6 | 100 ± 2 |
| (−) Sch B | 105 ± 41 | 137 ± 1** | 166 ± 4*** | 125 ± 5* | 171 ± 10*** | 178 ± 13** |
| α-LA | 101 ± 1 | 154 ± 12* | 123 ± 12 | 117 ± 5 | 171 ± 19*** | 147 ± 14* |
| α-Toc | 80 ± 8 | 153 ± 6** | 149 ± 8** | 136 ± 7** | 176 ± 13*** | 189 ± 11*** |

Animals were treated with (−) Sch B, α-lipoic acid (α-LA) or α-tocopherol (α-Toc) at a daily dose of 10, 5 and 70 mg/kg, respectively, for 15 days. Myocardial mitochondrial reduced glutathione (GSH) level and Se-glutathione peroxidase (GPX), glutathione reductase (GRD) and glutathione S-transferases (GST) activities were measured. Data were expressed as percent control. Values given are mean ± S.E.M., with n = 5. The number in the parentheses is the percent increase when compared with the respective untreated control.
*p < 0.05,
**p < 0.005 and
***p < 0.0005 when compared with the respected untreated control.

TABLE 6b

| | Heat Shock Protein Level (AU) | |
|---|---|---|
| | Hsp70 | Hsp25 |
| Brain | | |
| Control | 0.28 ± 0.02 | 0.10 ± 0.02 |
| (−) Sch B | 0.49 ± 0.05* (77%) | 0.16 ± 0.01 |
| Heart | | |
| Control | 0.61 ± 0.04 | 0.71 ± 0.03 |
| (−) Sch B | 0.71 ± 0.03* (17%) | 0.77 ± 0.05 |
| Liver | | |
| Control | 0.47 ± 0.04 | 0.35 ± 0.02 |
| (−) Sch B | 0.69 ± 0.001*** (45%) | 0.41 ± 0.02 |
| Skeletal Muscle | | |
| Control | 0.44 ± 0.01 | 0.54 ± 0.04 |
| (−) Sch B | 0.69 ± 0.07*** (57%) | 0.59 ± 0.03 |

Values given are mean ± S.E.M., with n = 5. The number in the parentheses is the percent increase when compared with the respective untreated control.
*$p < 0.05$,
**$p < 0.005$ and
***$p < 0.0005$ when compared with the respected untreated control Example 9

Preparation of Sport-Qi (SQ) Liquid (a) Preparation of Saponin-Containing Extract (SQ-I)

300 gram *Panax ginseng* Meyer and 900 gram *Ophiopogon japonica* Ker-Gawl powders were extracted by water (3 L, adjusted to pH 3.2 by adding citric acid) for 2 h under boiling and reflux conditions. The extraction procedure was repeated twice. The pooled extract was concentrated by rota-vaporation under reduced pressure to 1 L. The concentrated extract was precipitated by adding 2.8 L of 95% ethanol to make up a final concentration of ethanol of 70%. After removing the precipitates by filtration, the filtrate was concentrated by rota-vaporation under reduced pressure to obtain a paste, which was then dissolved in 750 ml water. This is the SQ-I. The total saponin content is determined using ginsenoside Re as standard.

(b) Preparation of Lignan-Containing Extract (SQ-II)

900 gram of *Schisandra* fruit powder was extracted by $CO_2$ supercritical fluid at 60° C. and 7500 psi. The restrictor was kept at 80° C., and the static extraction time was set at 5 min. The flow rate was 2 ml/min, and the dynamic extraction was maintained for 30 min. In each extraction, the extract was continuously collected in methanol during the dynamic extraction. Ethanol may be used in place of methanol to collect the extract when preparing a preparation for consumption or administration to a subject. The total lignans and (−) Schisandrin B content were measured by HPLC method.

(c) Reconstitution of Sport-Qi (SQ) Liquid

SQ-I (750 ml) was mixed with SQ-II (67 g). The pH of the mixture is adjusted to 7 by the addition of diluted hydrochloric acid. This is SQ liquid. On a concentration basis, the composition of SQ may vary as follows.

| | (mg/ml) | Preferred composition (mg/ml) |
|---|---|---|
| Total saponins | 6-15 | 6.0 |
| Total lignans | 1.0-2.0 | 1.0 |
| (−) Schisandrin B | 0.2-0.4 | 0.2 |

Example 10

Chemical Analysis of Sport-Qi (1) Total Saponins Content

The total saponin content of SQ-I was measured by the method of Hiai et al. (1975), using ginsengoside Re as standard.

(2) Total Lignans and (−) Schisandrin B Content

Total lignans and (−) Schisandrin B content of SQH was measured by an HPLC method, using $C_{18}$ NovaPak column (3.9 mm×150 mm). The mobile phase was 65% methanol (v/v, in $H_2O$) and eluted at 1 ml/min. The total lignan content was estimated using a (−) Schisandrin B standard.

The invention claimed is:

1. A method of enhancing physical performance in a subject during running exercise comprising administering to a subject in need thereof an effective amount of a composition comprising a Schisandrin B preparation, wherein the Schisandrin B preparation consists essentially of isolated (−) Schisandrin B.

2. The method of claim 1, wherein the concentration of (−) Schisandrin B in the composition is between about 0.01% and about 0.10% (w/w or w/v).

3. The method of claim 1, wherein the concentration of (−) Schisandrin B in the composition is between about 20% and about 40% (w/w or w/v).

4. The method of claim 1, wherein the composition further comprises at least one of a herbal extract, a fluid, a solvent, an antioxidant, a preservative, an electrolyte, a salt, and a pH control agent.

5. The method of claim 1, wherein the composition is an aqueous composition.

6. The method of claim 5, wherein the aqueous composition further comprises at least one of a saponin and a lignan, wherein the lignan is not (−) Schisandrin B.

7. The method of claim 6, wherein the aqueous composition comprises between about 0.5% and about 2% saponin, between about 0.05% and about 0.5% lignan, and between about 0.01% and about 0.1% (−) Schisandrin B.

8. The method of claim 7, wherein the aqueous composition comprises about 0.6% saponin (w/v), about 0.1% lignan (w/v), and about 0.02% (−) Schisandrin B (w/v).

\* \* \* \* \*